United States Patent

Minami et al.

Patent Number: 5,661,100
Date of Patent: Aug. 26, 1997

[54] UREA (THIOUREA) DERIVATIVE AND THERMAL RECORDING SHEET USING THE SAME

[75] Inventors: Toshiaki Minami; Tomoaki Nagai; Kaoru Hamada; Akio Sekine, all of Shinjuku-ku; Ryoichi Kinishi; Ryuzo Minakami, both of Fukuoka-ken, all of Japan

[73] Assignees: Nippon Paper Industries Co., Ltd., Tokyo; Yoshitomi Pharmaceutical Industries, Ltd., Osaka, both of Japan

[21] Appl. No.: 521,031

[22] Filed: Aug. 29, 1995

[30] Foreign Application Priority Data

Aug. 31, 1994 [JP] Japan .................. 6-206714

[51] Int. Cl.$^6$ .................................................. B41M 5/30
[52] U.S. Cl. .................... 503/209; 503/208; 503/216; 503/225
[58] Field of Search ............................. 503/208, 209, 503/216, 217, 225

[56] References Cited

U.S. PATENT DOCUMENTS

| 5,215,570 | 6/1993 | Burckhardt et la. | 504/104 |
| 5,292,711 | 3/1994 | Nishimura et al. | 503/209 |

FOREIGN PATENT DOCUMENTS

| 0521706 | 1/1993 | European Pat. Off. | 503/216 |
| 0611754 | 8/1994 | European Pat. Off. | 428/913 |
| 45-14039 | of 1970 | Japan | 503/217 |
| 49-109120 | 10/1974 | Japan | 503/221 |
| 59-106456 | 6/1984 | Japan | 503/216 |
| 59-116262 | 7/1984 | Japan | 503/216 |
| 59-190891 | 10/1984 | Japan | 503/221 |
| 60-13852 | 1/1985 | Japan | 503/216 |
| 4282291 | 10/1992 | Japan | 503/209 |
| 6227142 | 8/1994 | Japan | 503/216 |
| 6234273 | 8/1994 | Japan | 503/209 |
| 6234729 | 8/1994 | Japan | 503/209 |

OTHER PUBLICATIONS

Translation of the claim of Japanese Patent Publication No. 43-4160 (Feb. 15, 1968).
Database WPI Section Ch, Week 8713, Derwent Publ., Ltd., Abstract of JP-A-62-039277 (Feb. 20, 1987).
Patent Abstracts of Japan, vol. 8, No. 236 (C-249) (Oct. 30, 1984), Abstract of JP-A-59-116262 (Jul. 5, 1984).
Patent Abstracts of Japan, vol. 11, No. 228 (M-610) (Jul. 24, 1987), Abstract of JP-A-62-42883 (Feb. 24, 1987).
Ivanov, et al. "Production Of 1-Phenyl And 1-Alyl-3-Sulfanylamidothioureas", Comptes Rendus De L'Academie Bulgare Des Sciences, vol. 20, No. 7, 697-8 (1967).
Patent Abstracts of Japan, vol. 8, No. 22 (C-246) (Oct. 9, 1984), Abstract of JP-A-59-106456 (Jun. 20, 1984).

*Primary Examiner*—Bruce H. Hess
*Attorney, Agent, or Firm*—Sherman and Shalloway

[57] ABSTRACT

A thermal recording sheet wherein a compound of Formula (I) or (II) is contained in a thermal color developing layer including a basic colorless dye and an organic color developer as main ingredients:

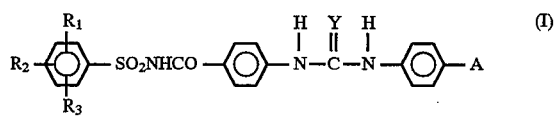

(wherein A denotes hydrogen atom, an alkyl group of $C_1$ to $C_4$, an alkoxy group of $C_1$ to $C_4$, hydroxy group, or nitro group. $R_1$, $R_2$, and $R_3$ are hydrogen atom, an alkyl group of $C_1$ to $C_4$, an alkoxy group of $C_1$ to $C_4$, hydroxy group, or nitro group. $R_1$ and $R_2$ may combine with each other to form an aromatic ring. Y is sulfur or oxygen atom.),

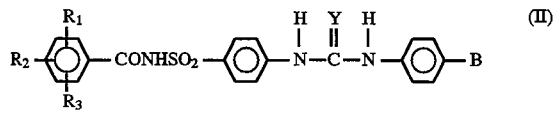

(wherein B denotes hydrogen atom, an alkyl group of $C_1$ to $C_4$, an alkoxy group of $C_1$ to $C_4$, hydroxy group, or nitro group. $R_1$, $R_2$, and $R_3$ are hydrogen atom, an alkyl group of $C_1$ to $C_4$, an alkoxy group of $C_1$ to $C_4$, hydroxy group, or nitro group. $R_1$ and $R_2$ may combine with each other to form an aromatic ring. Y is sulfur or oxygen atom.).

The thermal recording sheet has a high sensitivity and high image stability.

3 Claims, No Drawings

UREA (THIOUREA) DERIVATIVE AND THERMAL RECORDING SHEET USING THE SAME

FIELD OF THE INVENTION

This invention relates to a novel urea (thiourea) derivative and a thermal recording sheet using the compound.

BACKGROUND OF THE INVENTION

In general, a thermal recording sheet is obtained by mixing a normally colorless or pale colored dye precursor and a color developer such as a phenolic compound, each dispersed to fine particles and mixed, adding a binder, a filler, a sensitizer, a slip agent, and other additives to form a coating color, and coating the coating color on a substrate such as paper, synthetic paper, films, or plastics, which develops a color by a momentary chemical reaction caused by heating with a thermal head, a hot stamp, a thermal pen, laser light or the like to obtain a recorded image.

Thermal recording sheets are applied in a wide variety of areas such as measuring recorders, terminal printers for computers, facsimiles, automatic ticket venders, and bar code labels. However, with recent diversification of these recording devices and advance towards higher performance, quality requirements for thermal recording sheet have become higher and more difficult to achieve. For example, for high-speed recording, a thermal recording sheet which can provide a high recording density and a sharp recorded image even with a small thermal energy is in demand. On the other hand, in view of storage stability of the recording sheet, the thermal recording sheet is required to be superior in light resistance, weather resistance, and oil resistance.

Examples of conventional thermal recording sheets include, for example, a thermal recording material disclosed in Japanese Patent Publication 43-4160 or 45-14039. However, such conventional thermal recording materials have been low in thermal response and insufficient in color developing density when used in high-speed recording.

As methods for eliminating such disadvantages, high-sensitivity dyestuffs have been developed such as use of 3-N-methyl-N-cyclohexylamino-6-methyl-7-anilinofluorane (Japanese Patent Laid-open Publication (OPI) 49-109120) or 3-dibutylamino-6-methyl-7-anilinofluorane (Japanese OPI 59-190891) as a leuco dye, and as a color developer, use of 1,7-bis(4-hydroxyphenylthio)-3,5-dioxaheptane (Japanese OPI 59-106456), 1,5-bis(4-hydroxyphenylthio)-3-oxaheptane (Japanese OPI 59-116262), or 4-hydroxy-4'-isopropoxydiphenylsulfone (Japanese Patent Publication 63-46067) to achieve high-speed recording and high sensitivity.

However, although these thermal recording sheets have been high in sensitivity, have had a problem in thermal resistance in that when stored at high temperatures, they tend to result in a reduction of image density.

Further, since they are considerably low in storage stability of the recorded image, they still have disadvantages in that a considerable decrease in the image density or discoloration occurs when water or a sebaceous matter contacts the color image or the image contacts with a plasticizer (DOP, DOA, or the like) contained in wrap films such as PVC films.

Therefore, a primary object of the present invention is to provide a novel urea (thiourea) derivative and a thermal recording sheet with a high sensitivity and superior in thermal resistance, water resistance, and oil resistance by using the compound.

SUMMARY OF THE INVENTION

The novel urea (thiourea) compound of the present invention has a structure of Formula (I) or (II):

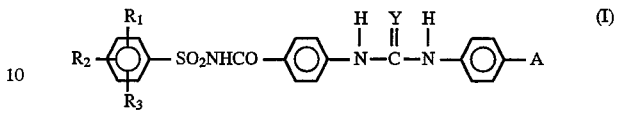

(wherein A denotes hydrogen atom, an alkyl group of $C_1$ to $C_4$, an alkoxy group of $C_1$ to $C_4$, hydroxy group, or nitro group. $R_1$, $R_2$, and $R_3$ are hydrogen atom, an alkyl group of $C_1$ to $C_4$, an alkoxy group of $C_1$ to $C_4$, hydroxy group, or nitro group. $R_1$ and $R_2$ may combine with each other to form an aromatic ring. Y is sulfur or oxygen atom.).

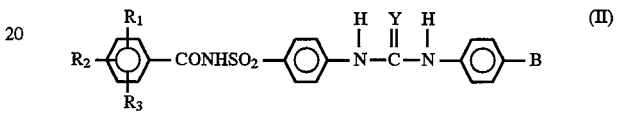

(wherein B denotes hydrogen atom, an alkyl group of $C_1$ to $C_4$, an alkoxy group of $C_1$ to $C_4$, hydroxy group, or nitro group. $R_1$, $R_2$, and $R_3$ are hydrogen atom, an alkyl group of $C_1$ to $C_4$, an alkoxy group of $C_1$ to $C_4$, hydroxy group, or nitro group. $R_1$ and $R_2$ may combine with each other to form an aromatic ring. Y is sulfur or oxygen atom.).

The present invention solves the above problems by containing a compound of Formula (I) or (II) in the thermal recording layer. That is, in the present invention, the compound of Formula (I) or (II) is used as an organic color developer to provide a superior color developing function. Since, when the compound is added to the thermal recording layer using another organic color developer, the recorded image is stable under extreme storage conditions, the compound can also be used as a stabilizer.

The novel compound of the present invention can be obtained by the method described in U.S. Pat. No. 2,383,874 in which the nitro group of N-arylsulfonyl-nitrobenzamide or N-acyl-nitrosulfamide is reduced to amino group, and then condensed with an isocyanate or thiocyanate. Specifically, the compound of the present invention includes the following compounds, which can be used alone or in combination of two or more types.

N-(benzenesulfonyl)-p-(phenylureilene)benzamide, N-(4-toluenesulfonyl)-p-(phenylureilene)benzamide, N-(4-ethylphenylsulfonyl)-p-(phenylureilene)benzamide, N-(4-n-propylphenylsulfonyl)-p-(phenylureilene)benzamide, N-(4-isopropylphenylsulfonyl)-p-(phenylureilene)benzamide, N-(4-t-butylphenylsulfonyl)-p-(phenylureilene)benzamide, N-(4-methoxyphenylsulfonyl)-p-(phenylureilene) benzamide, N-(4-ethoxyphenylsulfonyl)-p-(phenylureilene) benzamide, N-(4-hydroxyphenylsulfonyl)-p-(phenylureilene)benzamide, N-(2-hydroxyphenylsulfonyl)-p-(phenylureilene)benzamide, N-(4-nitrophenylsulfonyl)-p-(phenylureilene)benzamide, N-(benzenesulfonyl)-p-(4-tolylureilene)benzamide, N-(4-toluenesulfonyl)-p-(4-tolylureilene)benzamide, N-(4-ethylphenylsulfonyl)-p-(4-tolylureilene)benzamide, N-(4-isopropylsulfonyl)-p-(4-tolylureilene)benzamide, N-(4-butylphenylsulfonyl)-p-(4-tolylureilene)benzamide, N-(4-methoxyphenylsulfonyl)-p-(4-tolylureilene)benzamide, N-(4-hydroxyphenylsulfonyl)-p-(4-tolylureilene)benzamide, N-(2-hydroxyphenylsulfonyl)-p-(4-tolylureilene)benzamide, N-(4-nitrophenylsulfonyl)-p-(4-tolylureilene)benzamide, N-(benzenesulfonyl)-p-(2-naphthylureilene)benzamide, N-(4-toluenesulfonyl)-p-(2-naphthylureilene)benzamide, N-(4-isopropylsulfonyl)-p-(2-naphthylureilene)benzamide, N-(4-methoxyphenylsulfonyl)-p-(2-naphthylureilene) benzamide, N-(4-hydroxyphenylsulfonyl)-p-(2-naphthylureilene)benzamide, N-(4-nitrophenylsulfonyl)-p-(2-naphthylureilene)benzamide, N-(benzenesulfonyl)-p-(phenylthioureilene)benzamide, N-(4-toluenesulfonyl)-p-(phenylthioureilene)benzamide, N-(4-ethylphenylsulfonyl)-p-(phenylthioureilene)benzamide, N-(4-n-propylphenylsulfonyl)-p-(phenylthioureilene)benzamide, N-(4-isopropylphenylsulfonyl)-p-(phenylthioureilene) benzamide, N-(4-methoxyphenylsulfonyl)-p-(phenylthioureilene)benzamide, N-(4-ethoxyphenylsulfonyl)-p-(phenylthioureilene)benzamide, N-(4-hydroxyphenylsulfonyl)-p-(phenylthioureilene) benzamide, N-(2-hydroxyphenylsulfonyl)-p-(phenylthioureilene)benzamide, N-(4-nitrophenylsulfonyl)-p-(phenylthioureilene)benzamide, N-(benzenesulfonyl)-p-(4-tolylthioureilene)benzamide, N-(4-toluenesulfonyl)-p-(4-tolylthioureilene)benzamide, N-(4-n-propylphenylsulfonyl)-p-(4-tolylthioureilene)benzamide, N-(4-n-methoxyphenylsulfonyl)-p-(4-tolylthioureilene)benzamide, N-(4-methoxyphenylsulfonyl)-p-(4-methylphenylthioureilene) benzamide, N-(4-hydroxyphenylsulfonyl)-p-(4-tolylthioureilene)benzamide, N-(2-hydroxyphenylsulfonyl)-p-(4-methylphenylthioureilene)benzamide, N-(4-nitrophenylsulfonyl)-p-(4-methylphenylthioureilene)benzamide, N-(benzenesulfonyl)-p-(2-naphthylthioureilene) benzamide, N-(4-toluenesulfonyl)-p-(2-naphthylthioureilene) benzamide, N-(4-methoxyphenylsulfonyl)-p-(2-naphthylthioureilene) benzamide, N-(4-hydroxyphenylsulfonyl)-p-(2-naphthylthioureilene) benzamide, N-(2-hydroxyphenylsulfonyl)-p-(2-naphthylthioureilene) benzamide, N-(4-nitrophenylsulfonyl)-p-(2-naphthylthioureilene)benzamide, N-(phenyl)-N'-(p-benzoylaminosulfonyl)phenylurea, N-(phenyl)-N'-{p-(4-toluoylaminosulfonyl)}phenylurea, N-(phenyl)-N'-{p-(2-naphthoylaminosulfonyl)}phenylurea, N-(phenyl)-N'-{p-(4-hydroxybenzoylaminosulfonyl)}phenylurea, N-(phenyl)-N'-{p-(2-hydroxybenzoylaminosulfonyl)}phenylurea, N-(phenyl)-N'-{p-(4-methoxybenzoylaminosulfonyl)} phenylurea, N-(phenyl)-N'-{p-(4-ethoxybenzoylaminosulfonyl)}phenylurea, N-(phenyl)-N'-{p-(4-n-propoxybenzoylaminosulfonyl)}phenylurea, N-(phenyl)-N'-{p-(4-isopropoxybenzoylaminosulfonyl)} phenylurea, N-(Phenyl)-N'-{p-(4-nitrobenzoylaminosulfonyl)}phenylurea, N-(4-toluyl)-N'-{p-(benzoylaminosulfonyl)}phenylurea, N-(4-toluyl)-N'-{p-(4-toluoylaminosulfonyl)}phenylurea, N-(4-toluyl)-N'-{p-(2-naphthoylaminosulfonyl)}phenylurea, N-(3-toluyl)-N'-(p-benzoylaminosulfonyl)phenylurea, N-(3-toluyl)-N'-{p-(4-toluoylaminosulfonyl)}phenylurea, N-(3-toluyl)-N'-{p-(3-toluoylaminosulfonyl)}phenylurea, N-(3-toluyl)-N'-{p-(2-toluoylaminosulfonyl)}phenylurea, N-(3-toluyl)-N'-{p-(2-naphthoylaminosulfonyl)phenylurea, N-(4-toluyl)-N'-{p-(4-hydroxybenzoylaminosulfonyl)}phenylurea, N-(4-toluyl)-N'-{p-(2-hydroxybenzoylaminosulfonyl)} phenylurea, N-(4-toluyl)-N'-{p-(4-methoxybenzoylaminosulfonyl)}phenylurea, N-(4-toluyl)-N'-{p-(4-nitrobenzoylaminosulfonyl)}phenylurea, N-(phenyl)-N'-{p-(4-toluoylaminosulfonyl)} phenylthiourea, N-(phenyl)-N'-{p-(2-naphthoylaminosulfonyl)}phenylthiourea, N-(phenyl)-N'-{p-(4-hydroxybenzoylaminosulfonyl)}phenylthiourea, N-(phenyl)-N'-{p-(4-methoxybenzoylaminosulfonyl)} phenylthiourea, N-(phenyl)-N'-{p-(4-nitrobenzoylaminosulfonyl)}phenylthiourea, N-(4-toluyl)-N'-{p-(4-toluoylaminosulfonyl)}phenylthiourea, N-(4-toluyl)-N'-{p-(3-toluoylaminosulfonyl)}phenylthiourea, N-(4-toluyl)-N'-{p-(2-naphthoylaminosulfonyl)} phenylthiourea, N-(3-toluyl)-N'-{p-(benzoylaminosulfonyl)}phenylthiourea, N-(3-toluyl)-N'-(p-benzoylaminosulfonyl)}phenylthiourea, N-(3-toluyl)-N'-{p-(3-toluoylaminosulfonyl)}phenylthiourea, N-(3-toluyl)-N'-{p-(2-naphthoylaminosulfonyl)}phenylthiourea, N-(4-toluyl)-N'-{p-(4-hydroxybenzoylaminosulfonyl)} phenylthiourea, N-(4-toluyl)-N'-{p-(4-methoxybenzoylaminosulfonyl)}phenylthiourea, N-(4-toluyl)-N'-{p-(4-nitrobenzoylaminosulfonyl)}phenylthiourea.

In the present invention, the compound of Formula (1) can of course be used as a color developer and, in this case, one or more types of other organic color developers can be used in combination as far as the advantages of the compound of the present invention are not impaired. Other organic color developers include the following bisphenols A, 4-hydroxybenzoic acid esters, 4-hydroxyphthalic acid diesters, phthalic acid monoesters, bis-(hydroxyphenyl) sulfides, 4-hydroxyphenylarylsulfones, 4-hydroxyphenylarylsulfonates, 1,3-di[2-(hydroxyphenyl)-2-propyl]-benzenes, 4-hydroxybenzoyloxybenzoic acid esters, and bisphenolsulfones. Further, in the present invention, the above-described other organic color developers can be used alone or in combination of two or more types, and the compound of Formula (II) can also be used as a stabilizer. Practical examples of other organic color developers are shown below:

<Bisphenols A>

4,4'-Isopropylidene-diphenol (Bisphenol A)

4,4'-Cyclohexylidene-diphenol p,p'-(1-Methyl-n-hexylidene)-diphenol 1,7-Di(4-hydroxyphenylthio)-3,5-dioxaheptane <4-Hydroxybenzoic acid esters>

Benzyl 4-hydroxybenzoate

Ethyl 4-hydroxybenzoate

Propyl 4-hydroxybenzoate

Isopropyl 4-hydroxybenzoate

Butyl 4-hydroxybenzoate

Isobutyl 4-hydroxybenzoate

Methylbenzyl 4-hydroxybenzoate

<4-Hydroxyphthalic acid diesters>

Dimethyl 4-hydroxyphthalate

Diisopropyl 4-hydroxyphthalate

Dibenzyl 4-hydroxyphthalate

Dihexyl 4-hydroxyphthalate

<Phthalic Acid Monoesters>

Monobenzyl phthalate

Monocyclohexyl phthalate

Monophenyl phthalate

Monomethylphenyl phthalate

Monoethylphenyl phthalate

Monopropylbenzyl phthalate

Monohalogenbenzyl phthalate

Monoethoxybenzyl phthalate

<Bis-(hydroxyphenyl)-sulfides>

Bis-(4-hydroxy-3-tert-butyl-6-methylphenyl)sulfide

Bis-(4-hydroxy-2,5-dimethylphenyl)sulfide

Bis-(4-hydroxy-2-methyl-5-ethylphenyl)sulfide
Bis-(4-hydroxy-2-methyl-5-isopropylphenyl)sulfide
Bis-(4-hydroxy-2,3-dimethylphenyl)sulfide
Bis-(4-hydroxy-2,5-dimethylphenyl)sulfide
Bis-(4-hydroxy-2,5-diisopropylphenyl)sulfide
Bis-(4-hydroxy-2,3,6-trimethylphenyl)sulfide
Bis-(2,4,5-trihydroxyphenyl)sulfide
Bis-(4-hydroxy-2-cyclohexyl-5-methylphenyl)sulfide
Bis-(2,3,4-trihydroxyphenyl)sulfide
Bis-(4,5-dihydroxy-2-tert-butylphenyl)sulfide
Bis-(4-hydroxy-2,5-diphenylphenyl)sulfide
Bis-(4-hydroxy-2-tert-octyl-5-methylphenyl)sulfide
<4-Hydroxyphenylarylsulfones>
  4-Hydroxy-4'-isopropoxydiphenylsulfone
  4-Hydroxy-4'-propoxydiphenylsulfone
  4-Hydroxy-4'-n-butyloxydiphenylsulfone
  4-Hydroxy-4'-n-propoxydiphenylsulfone
<4-Hydroxyphenylarylsulfonates>
  4-Hydroxyphenylbenzenesulfonate
  4-Hydroxyphenyl-p-tolylsulfonate
  4-Hydroxyphenylbenzenesulfonate
  4-Hydroxyphenyl-p-chlorobenzenesulfonate
  4-Hydroxyphenyl-p-tert-butylbenzenesulfonate
  4-Hydroxyphenyl-p-isopropoxybenzenesulfonate
  4-Hydroxyphenyl-1'-naphthalenesulfonate
  4-Hydroxyphenyl-2'-naphthalenesulfonate
<1,3-Di[2-(4-hydroxyphenyl)-2-propyl]-benzenes>
  1,3-Di[2-(4-hydroxyphenyl)-2-propyl]-benzene
  1,3-Di[2-(4-hydroxy-3-alkylphenyl)-2-propyl]-benzene
  1,3-Di[2-(2,4-dihydroxyphenyl)-2-propyl]-benzene
  1,3-Di[2-(2-hydroxy-5-methylphenyl)-2-propyl]-benzene
<Resorcinols>
  1,3-Dihydroxy-6-(α,α-dimethylbenzyl)-benzene
<4-Hydroxybenzoyloxybenzoic acid esters>
  Benzyl 4-hydroxybenzoyloxybenzoate
  Methyl 4-hydroxybenzoyloxybenzoate
  Ethyl 4-hydroxybenzoyloxybenzoate
  Propyl 4-hydroxybenzoyloxybenzoate
  Butyl 4-hydroxybenzoyloxybenzoate
  Isopropyl 4-hydroxybenzoyloxybenzoate
  tert-Butyl 4-hydroxybenzoyloxybenzoate
  Hexyl 4-hydroxybenzoyloxybenzoate
  Octyl 4-hydroxybenzoyloxybenzoate
  Nonyl 4-hydroxybenzoyloxybenzoate
  Cyclohexyl 4-hydroxybenzoyloxybenzoate
  β-Phenethyl 4-hydroxybenzoyloxybenzoate
  Phenyl 4-hydroxybenzoyloxybenzoate
  α-Naphthyl 4-hydroxybenzoyloxybenzoate
  β-Naphthyl 4-hydroxybenzoyloxybenzoate
  sec-Butyl 4-hydroxybenzoyloxybenzoate
<Bisphenolsulfones (I)>
  Bis-(3-1-butyl-4-hydroxy-6-methylphenyl)sulfone
  Bis-(3-ethyl-4-hydroxyphenyl)sulfone
  Bis-(3-propyl-4-hydroxyphenyl)sulfone
  Bis-(3-methyl-4-hydroxyphenyl)sulfone
  Bis-(3-isopropyl-4-hydroxyphenyl)sulfone
  Bis-(2-ethyl-4-hydroxyphenyl)sulfone
  Bis-(3-chloro-4-hydroxyphenyl)sulfone
  Bis-(2,3-dimethyl-4-hydroxyphenyl)sulfone
  Bis-(2,5-dimethyl-4-hydroxyphenyl)sulfone
  Bis-(3-methoxy-4-hydroxyphenyl)sulfone
  4-Hydroxyphenyl-2'-ethyl-4'-hydroxyphenylsulfone
  4-Hydroxyphenyl-2'-isopropyl-4'-hydroxyphenylsulfone
  4-Hydroxyphenyl-3'-isopropyl-4'-hydroxyphenylsulfone
  4-Hydroxyphenyl-3'-sec-butyl-4'-hydroxyphenylsulfone
  3-Chloro-4-hydroxyphenyl-3'-isopropyl-4'-hydroxyphenylsulfone
  2-Hydroxy-5-t-butylphenyl-4'-hydroxyphenylsulfone
  2-Hydroxy-5-t-aminophenyl-4'-hydroxyphenylsulfone
  2-Hydroxy-5-t-isopropylphenyl-4'-hydroxyphenylsulfone
  2-Hydroxy-5-t-octylphenyl-4'-hydroxyphenylsulfone
  2-Hydroxy-5-t-butylphenyl-3'-chloro-4'-hydroxyphenylsulfone
  2-Hydroxy-5-t-butylphenyl-3'-methyl-4'-hydroxyphenylsulfone
  2-Hydroxy-5-t-butylphenyl-3'-isopropyl-4'-hydroxyphenylsulfone
  2-Hydroxy-5-t-butylphenyl-3'-chloro-4'-hydroxyphenylsulfone
  2-Hydroxy-5-t-butylphenyl-3'-methyl-4'-hydroxyphenylsulfone
  2-Hydroxy-5-t-butylphenyl-3'-isopropyl-4'-hydroxyphenylsulfone
  2-Hydroxy-5-t-butylphenyl-3'-methyl-4'-hydroxyphenylsulfone.
<Bisphenolsulfones (II)>
  4,4'-Sulfonyldiphenol
  2,4'-Sulfonyldiphenol
  3,3'-Dichloro-4,4'-sulfonyldiphenol
  3,3'-Dibromo-4,4'-sulfonyldiphenol
  3,3',5,5'-Tetrabromo-4,4'-sulfonyldiphenol
  3,3'-Diamino-4,4'-sulfonyldiphenol
<Others>
  p-tert-Butylphenol
  2,4-Dihydroxybenzophenone
  Novolac type phenolic resin
  4-Hydroxyacetophenone
  p-Phenylphenol
  Benzyl 4-hydroxyphenylacetate
  p-Benzylphenol The basic colorless dyes used in the present invention are not specifically limited, but triphenylmethane type compounds, fluorane type compounds, fluorene type compounds, and divinyl type compounds are preferable. Typical examples of these dyes are shown below. These dyes may be used alone or in combination of two or more types.
<Triphenylmethane type leuco dyes>
  3,3-Bis(p-dimethylaminophenyl)-6-dimethylaminophthalide [Crystal Violet Lactone]
<Fluorane type leuco dyes (I)>
  3-Diethylamino-6-methyl-7-anilinofluorane
  3-(N-ethyl-p-toluidino)-6-methyl-7-anilinofluorane
  3-(N-ethyl-N-isoamylamino)-6-methyl-7-anilino)fluorane
  3-Diethylamino-6-methyl-7-(o,p-dimethylanilino)fluorane 3-Pyrrolidino-6-methyl-7-anilinofluorane
3-Piperidino-6-methyl-7-anilinofluorane
3-(N-cyclohexyl-N-methylamino)-6-methyl-7-anilinofluorane
3-Diethylamino-7-(m-trifluoromethylanilino)fluorane
3-N-n-dibutylamino-6-methyl-7-anilinofluorane
3-N-n-dibutylamino-7-(o-chloroanilino)fluorane
3-(N-ethyl-N-tetrahydrofurfurylamino)-6-methyl-7-anilinofluorane
3-Dibutylamino-6-methyl-7-(o,p-dimethylanilino)fluorane
3-(N-methyl-N-propylamino)-6-methyl-7-anilinofluorane
3-Diethylamino-6-chloro-7-anilinofluorane
3-Dibutylamino-7-(o-chloroanilino)fluorane
3-Diethylamino-7-(o-chloroanilino)fluorane
3-Diethylamino-6-methyl-chlorofluorane
3-Diethylamino-6-methyl-fluorane
3-Cyclohexylamino-6-chlorofluorane
3-Diethylamino-benzo[a]fluorane
3-n-Dipentylamino-6-methyl-7-anilinofluorane
2-(4-Oxo-hexyl)-3-dimethylamino-6-methyl-7-anilinofluorane
2-(4-Oxo-hexyl)-3-diethylamino-6-methyl-7-anilinofluorane
2-(4-Oxo-hexyl)-3-dipropylamino-6-methyl-7-anilinofluorane <Fluorene type leuco dyes>

3,6,6'-Tris(dimethylamino)spiro[fluorene-9,3'-phthalide]
3,6,6'-Tris(diethylamino)spiro[fluorene-9,3'-phthalide]

<Fluorane type leuco dyes (II)>

2-Methyl-6-p-(p-dimethylaminophenyl)aminoanilinofluorane
2-Methoxy-6-p-(p-dimethylaminophenyl)aminoanilinofluorane
2-Chloro-3-methyl-6-p-(p-phenylaminophenyl)aminoanilinofluorane
2-Chloro-6-p-(p-dimethylaminophenyl)aminoanilinofluorane
2Nitro-6-p-(p-diethylaminophenyl)aminoanilinofluorane
2-Amino-6-p-(p-diethylaminophenyl)aminoanilinofluorane
2-Diethylamino-6-p-(p-diethylaminophenyl)aminoanilinofluorane
2-Phenyl-6-methyl-p-(p-phenylaminophenyl)aminoanilinofluorane
2-Benzyl-6-p-(p-phenylaminophenyl)aminoanilinofluorane
2-Hydroxy-6-p-(p-phenylaminophenyl)aminoanilinofluorane
3-Methyl-6-p-(p-dimethylaminophenyl)aminoanilinofluorane
3-Diethylamino-6-p-(p-diethylaminophenyl)aminoanilinofluorane
3-Diethylamino-6-p-(p-dibutylaminophenyl)aminoanilinofluorane <Divinyl type leuco dyes>

3,3-Bis-[2-(p-dimethylaminophenyl)-2-(p-methoxyphenyl) ethenyl]-4,5,6,7-tetrabromophthalide
3,3-Bis-[2-(p-dimethylaminophenyl)-2-(p-methoxyphenyl) ethenyl]-4,5,6,7-tetrachlorophthalide
3,3-Bis-[1,1-bis(4-pyrrolidinophenyl)-2-(p-methoxyphenyl) ethylen-2-yl]-4,5,6,7-tetrabromophthalide
3,3-Bis-[1-(4-methoxyphenyl)-1-(4-pyrrolidinophenyl)ethylen-2-yl]-4,5,6,7-tetrachlorophthalide <Others>

1,1-Bis-[2',2',2",2"-tetrakis-(p-dimethylaminophenyl)-ethenyl]-2,2-dinitrileethane
1,1-Bis-[2 ,2',2",2"-tetrakis-(p-dimethylaminophenyl)-ethenyl]-2,2-naphthoyleethane
1,1-Bis-[2 ,2',2",2"-tetrakis-(p-dimethylaminophenyl)-ethenyl]-2,2-diacetylethane
Bis-[2,2,2,2'-tetrakis-(p-dimethylaminophenyl)-ethenyl]-methylmalonic acid dimethyl ester.

Further, as a sensitizer, a fatty acid amide such as stearamide or palmitamide; ethylene-bisamide, montan wax, polyethylene wax, dibenzyl terephthalate, benzyl p-benzyloxybenzoate, di-p-tolylcarbonate, p-benzylbiphenyl, phenyl-α-naphthylcarbonate, 1,4-diethoxynaphthalene, 1-hydroxy-2-naphthoic acid phenyl ester, 1,2-di-(3-methylphenoxy)ethane, di(p-methylbenzyl) oxalate, β-benzyloxynaphthalene, 4-biphenyl-p-tolylether, o-xylylene-bis-(phenylether), 4-(m-methylphenoxymethyl) biphenyl, or the like can be added.

The binder used in the present invention includes completely-hydrolyzed polyvinylalcohol having a polymerization degree of 200 to 1900, partially-hydrolyzed polyvinylalcohol, carboxy-modified polyvinylalcohol, amide-modified polyvinylalcohol, sulfonic acid-modified polyvinylalcohol, butyral-modified polyvinylalcohol, other modified polyvinylalcohols, hydroxyethylcellulose, methylcellulose, carboxymethylcellulose, styrene-maleic anhydride copolymer, styrene-maleic anhydride copolymer, styrene-butadiene copolymer, cellulose derivatives such as ethylcellulose and acetylcellulose, polyvinylchloride, polyvinylacetate, polyacrylamide, polyacrylic acid esters, polyvinylbutyral, polystyrene, and copolymers thereof, polyamide resins, silicone resins, petroleum resins, terpene resins, ketone resins, and coumarone resins. These polymeric substances are used by dissolving in solvents such as water, alcohol, ketone, ester, and hydrocarbon, emulsifying or dispersing to a paste form in water or other solvents, and can be used in combination according to the quality requirements.

In the present invention, it is also possible to add known stabilizers based on metal salts (Ca, Zn) of p-nitrobenzoic acid or metal salts (Ca, Zn) of phthalic acid monobenzyl ester, as much as the desired effect of the present invention is not hindered.

Fillers that can be used in the present invention include inorganic or organic fillers such as such as silica, calcium carbonate, kaolin, calcined kaolin, diatomaceous earth, talc, and titanium oxide.

In addition to the above, it is also possible to use release agents such as fatty acid metal salts, slip agents such as waxes, benzophenone- or triazole-based ultraviolet absorbers, water resistant agents such as glyoxal, dispersants, defoamers, antioxidants, and the like.

The amounts of the color developer and the basic colorless dye used in the present invention and the types and amounts of other constituents are determined according to the required properties and recording adaptability, and are not specifically limited, but when the compound of the present invention is used as the color developer, it is usually preferable to use 1 to 8 parts of the color developer and 1 to 20 parts of the filler to 1 part of the basic colorless dye, and the binder is used in an amount of 10 to 25% of the total solid. When the compound of the present invention is used as a stabilizer, it is preferable to use 1 to 8 parts of the color developer, 0.25 to 3 parts of the stabilizer, and 1 to 20 parts of the filler to 1 part of the basic colorless dye, and the binder is used in an amount of 10 to 25% of the total solid.

The coating color of the above composition is coated on any type of substrate such as paper, synthetic paper, plastic films, non-woven fabrics, or metal foils to obtain the objective thermal recording sheet.

Furthermore, the sheet can be provided with an overcoating layer comprising a polymeric substance on the thermal color developing layer to improve the storage stability. Or, to enhance the storage stability and sensitivity, an undercoating layer containing an organic or inorganic filler can be provided under the thermal color developing layer.

The organic color developer, the basic colorless dye, and the materials which are added as necessary are finely divided by a grinding machine such as a ball mill, an attriter, or a sand grinder, or by an appropriate emulsifying apparatus, to a particle diameter of less than several microns, and mixed with the binder and various additives according to the purpose to obtain a coating color.

The reason why the effect of the present invention is obtained when the specific compound of the present invention is used can be considered as follows.

The reason for the high thermal resistance, water resistance, and oil resistance of the recorded image is explained as follows. In general, a thermal recording paper comprises a basic colorless dye as an electron donor, and an organic acid substance such as phenolic compound, aromatic carboxylic acid, or organic sulfonic acid as an electron acceptor. The heat melting reaction of the basic colorless dye and the color developer is an acid-base reaction based on the donation and acceptance of electron, which forms a meta-stable "charge transfer complex" to obtain a colored image. At this moment, since the compound of the present invention has a so-called acidified nitrogen atom having a reduced electron density adjacent to the electron attracting group in the molecule, the chemical binding force of acid and base is enhanced and, as a result, the recorded image is stabilized by a reaction of the color developer and the leuco dye during the heat melting reaction, and the stability of the color developed image is maintained even under an environment where the recorded image is exposed to water, oil, or heat.

DETAILED DESCRIPTION OF EXAMPLES

The present invention will be described with reference to the examples. In the description, part indicates part by weight unless otherwise noted.

SYNTHESIS EXAMPLE 1

Synthesis of N-(benzenesulfonyl)-p-(phenylureilene) benzamide

In a 300-ml reaction flask provided with a thermometer and a stirrer, 18.5 g of p-nitrobenzoyl chloride, 15.7 g of benzenesulfonamide, 100 g of tolueene, and 8 g of pyridine were charged, and reacted at 100° C. for 5 hours. After the reaction, the reaction mixture was cooled, was added, and the internal temperature was decreased to 30° C. to sufficiently precipitate crystals. The solution was filtered to obtain 27.2 g of N-(benzenesulfonyl)-p-nitrobenzamide.

27.2 g of the thus obtained N-(benzenesulfonyl)-p-nitrobenzamide, 270 g of water, and 5.4 g of glacial acetic acid were charged in a 1,000-ml reaction flask, 54 g of iron powder was slowly added, and a reductive reaction was carried out for 12 hours. The reaction solution was made alkaline with sodium carbonate and filtered. The transparent filtrate was acidified with acetic acid to obtain 19.8 g of N-(benzenesulfonyl)-p-aminobenzamide.

19.8 g of N-(benzenesulfonyl)-p-aminobenzamide, 50 g of 1,2-dichloromethane, and 10 g of phenylisocyanate were charged in a 300-ml reaction flask, and reacted for 6 hours at room temperature. Then, 50-ml of water was added, stirred for 1 hour, and a crystal was filtered. The crystal was recrystallized from a water-methanol mixture to obtain 24.5 go of N-(benzenesulfonyl)-p-(phenylureilene)benzamide (Formula III).

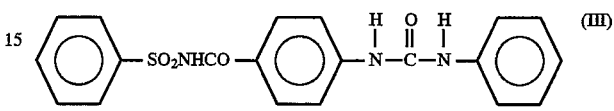

SYNTHESIS EXAMPLE 2

Synthesis of N-(4-toluenesulfonyl)-p-(phenylureilene) benzamide 18.5 Grams of p-nitrobenzoyl chloride, 17.1 g of 4-toluenesulfonamide, 100 g of toluene, and 8 g of pyridine were charged in a reaction vessel, and reacted using the same procedure as in Synthesis Example 1 to obtain 26.7 g of N-(4-toluenesulfonyl)-p-(phenylureilene)benzamide as a white crystal having a melting point of 223° (Formula IV).

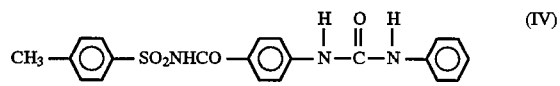

SYNTHESIS EXAMPLE 3

Synthesis of N-(benzenesulfonyl)-p-(phenylthioureilene) benzamide 20.0 Grams of N-(4-toluenesulfonyl)-p-nitrobenzamide synthesized by the method of Synthesis Example 1 and 80 g of N,N-dimethylformamide were charged in a 300-ml with a dropping funnel and thoroughly dissolved, 12 g of phenylisothiocyanate was dropped therein and reacted for 6 hours. Then, 150 g of water and 30 g of toluene were added and thoroughly stirred to precipitate a crystal. The crystal was filtered and dissolved in methanol at room temperature, and diluted with a small amount of water to precipitate 20.5 g crystal of N-(benzenesulfonyl)-p-(phenylthioureilene) benzamide having a melting point of 170° C. (Formula V).

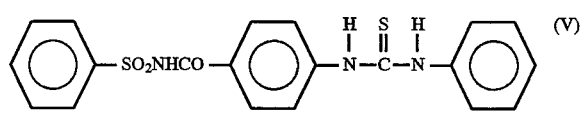

SYNTHESIS EXAMPLE 4

Synthesis of N-(4-toluenesulfonyl)-p-(phenylthioureilene) benzamide

Using the same procedure as in Synthesis Example 1, 20 g of N-(4-toluenesulfonyl)-p-nitrobenzamide obtained in Synthesis Example and 12 g of phenylisothiocyanate were charged and reacted using the same procedure as in Synthesis Example 3 to obtain 23.2 g of N-(4-toluenesulfonyl-p-(phenylthioureilene)benzamide having a melting point of 175° C. (Formula VI).

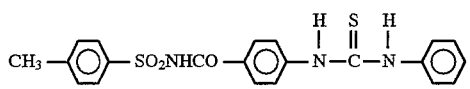

SYNTHESIS EXAMPLE 5

Synthesis of N-(phenyl)-N'-{p-(benzoylaminosulfonyl)} phenylurea

In a reaction flask with a thermometer and a stirrer, 25 g of p-nitrobenzenesulfonamide, 18 g of benzoylchloride, 1 g of copper powder, and 100 g of toluene were charged and refluxed until evolution of hydrogen chloride gas was completely ended. The reaction mixture was then cooled to room temperature to precipitate a crystal, which was filtered. The crystal was dissolved in an aqueous sodium carbonate solution and filtered. The filtrate was neutralized with hydrochloric acid to precipitate a crystal. The crystal was filtered to obtain 30.6 g of N-(4-nitrobenzenesulfonyl)benzamide.

30.6 Grams of the N-(4-nitrobenzenesulfonyl)benzamide was reduced using the same procedure as in Synthesis Example 1 to obtain 20.4 g of N-(4-aminobenzenesulfonyl) benzamide. Further, using the same procedure as in Synthesis Example 1, it is reacted with 10 g of phenylisocyanate to obtain 21.3 g of N-(phenyl)-N'-{p-(benzoylaminosulfonyl)} phenylurea having a melting point of 231.5° C. (Formula VII).

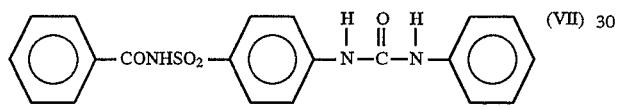

SYNTHESIS EXAMPLE 6

Synthesis of N-(phenyl)-N'-{p-(benzoylaminosulfonyl)} phenylthiourea 20.0 Grams of N-(4-aminobenzenesulfonyl)benzamide obtained according to Synthesis Example 5, 12.0 g of phenylisothiocyanate, and 80 g of N,N-dimethylformamide were charged in a reaction flask, and reacted using the same procedure as in Synthesis Example 3 to obtain 18.2 g of N-(phenyl)-N'-{p-(benzoylaminosulfonyl)}phenylthiourea having a melting point of 179° C. (Formula VIII).

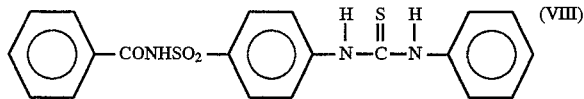

Examples for producing a thermal recording sheet using the compound of the present invention will be described.

EXAMPLE 1 (Test Nos. 1–32)

| Liquid A (color developer dispersion) | |
|---|---|
| Color developer (see Tables 1 and 2) | 6.0 parts |
| 10% Aqueous polyvinylalcohol solution | 18.8 |
| Water | 11.2 |
| Liquid B (dye dispersion) | |
| 3-(N-ethyl-N-isoamylamino)-6-methyl-7-anilinofluorane | 2.0 parts |
| 10% Aqueous polyvinylalcohol solution | 4.6 |
| Water | 2.6 |
| Liquid C (sensitizer dispersion) | |
| 4-Biphenyl-p-tolylether | 4.0 parts |
| 10% Aqueous polyvinylalcohol solution | 5.0 |
| Water | 3.0 |

The liquids of the above compositions were milled by a sand grinder to an average particle diameter of 1 micron, and mixed in the following ratio to obtain a coating color.

| Liquid A | 36.0 parts |
|---|---|
| Liquid B | 9.2 |
| Liquid C | 12.0 |
| Kaolin clay (50% dispersion) | 12.0 |

The coating color was coated on one side of a 50 g/m² base paper to a coating amount of 6.0 g/m², dried, and supercalendered to a flatness of 500 to 600 seconds to obtain a thermal recording sheet.

COMPARATIVE EXAMPLE 1 (Test Nos. 33–38)

| Liquid D (color developer dispersion) | |
|---|---|
| Color developer (see Table 5) | 6.0 parts |
| 10% Aqueous polyvinylalcohol solution | 18.8 |
| Water | 11.2 |
| Liquid B (dye dispersion) | |
| 3-(N-ethyl-N-isoamylamino)-6-methyl-7-anilinofluorane | 2.0 parts |
| 10% Aqueous polyvinylalcohol solution | 4.6 |
| Water | 2.6 |
| Liquid C (sensitizer dispersion) | |
| 4-Biphenyl-p-tolylether | 4.0 parts |
| 10% Aqueous polyvinylalcohol solution | 5.0 |
| Water | 3.0 |

The liquids of the above compositions were milled by a sand grinder to an average particle diameter of 1 micron, mixed in the following ratio to obtain a coating color, and treated as in Example 1 to obtain a thermal recording sheet.

| Liquid D | 36.0 parts |
|---|---|
| Liquid B | 9.2 |
| Liquid C | 12.0 |
| Kaolin clay (50% dispersion) | 12.0 |

EXAMPLE 2 (Test Nos. 39–41)

| Liquid E (color developer dispersion) | |
|---|---|
| Color developer (see Table 7) | 6.0 parts |
| 10% Aqueous polyvinylalcohol solution | 18.8 |
| Water | 11.2 |
| Liquid B (dye dispersion) | |
| 3-(N-ethyl-N-isoamylamino)-6-methyl-7-anilinofluorane | 2.0 parts |
| 10% Aqueous polyvinylalcohol solution | 4.6 |
| Water | 2.6 |
| Liquid C (sensitizer dispersion) | |
| 4-Biphenyl-p-tolylether | 4.0 parts |
| 10% Aqueous polyvinylalcohol solution | 5.0 |

-continued

| | | |
|---|---|---|
| Water | 3.0 | |
| Liquid F (stabilizer dispersion) | | |
| Stabilizer (see Table 7) | 2.0 | parts |
| 10% Aqueous polyvinylalcohol solution | 2.5 | |
| Water | 1.5 | |

The liquids of the above compositions were milled by a sand grinder to an average particle diameter of 1 micron, mixed in the following ratio to obtain a coating color, and treated as in Example 1 to obtain a thermal recording sheet.

| | | |
|---|---|---|
| Liquid E | 36.0 | parts |
| Liquid B | 9.2 | |
| Liquid C | 12.0 | |
| Liquid F | 6.0 | |
| Kaolin clay (50% dispersion) | 12.0 | |

The thermal recording sheets obtained in the above Examples and Comparative Example were subjected to quality evaluation tests. The tests results are shown in Tables 1–8.

TABLE 1

Quality test results

| Test No. | Color developer |
|---|---|
| Example 1 | |
| 1 (Synth. Ex. 1) | N-(benzenesulfonyl)-p-(phenylureilene)benzamide |
| 2 (Synth. Ex. 2) | N-(4-toluenesulfonyl)-p-(phenylureilene)benzamide |
| 3 (Synth. Ex. 3) | N-(benzenesulfonyl)-p-(phenylthioureilene)benzamide |
| 4 (Synth. Ex. 4) | N-(4-toluenesulfonyl)-p-(phenylthioureilene)benzamide |
| 5 | N-(4-methoxyphenylsulfonyl)-p-(phenylureilene)benzamide |
| 6 | N-(2-hydroxyphenylsulfonyl)-p-(phenylureilene)benzamide |
| 7 | N-(4-toluenesulfonyl)-p-(4-tolylureilene)benzamide |
| 8 | N-(n-butylphenylsulfonyl)-p-(4-tolylureilene)benzamide |
| 9 | N-(2-hydroxyphenylsulfonyl)-p-(4-tolylureilene)benzamide |
| 10 | N-(4-toluenesulfonyl)-p-(2-naphthylureilene)benzamide |
| 11 | N-(4-hydroxyphenylsulfonyl)-p-(2-naphthylureilene)benzamide |

TABLE 1-continued

Quality test results

| Test No. | Color developer |
|---|---|
| 12 | N-(4-toluenesulfonyl)-p-(phenylthioureilene)benzamide |
| 13 | N-(4-isopropylphenylsulfonyl)-p-(phenylthioureilene)benzamide |
| 14 | N-(4-hydroxyphenylsulfonyl)-p-(phenylthioureilene)benzamide |
| 15 | N-(benzenesulfonyl)-p-(4-tolylthioureilene)benzamide |
| 16 | N-(4-methoxyphenylsulfonyl)-p-(4-methylphenylthioureilene)benzamide |

TABLE 2

Quality test results

| Test No. | Color developer |
|---|---|
| Example 1 | |
| 17 (Synth. Ex. 5) | N-(phenyl)-N'-(p-benzoylaminosulfonyl)phenylurea |
| 18 (Synth. Ex. 6) | N-(phenyl)-N'-(p-benzoylaminosulfonyl)phenylthiourea |
| 19 | N-(phenyl)-N'-{p-(4-hydroxybenzoylaminosulfonyl)}phenylurea |
| 20 | N-(phenyl)-N'-{p-(4-ethoxybenzoylaminosulfonyl)}phenylurea |
| 21 | N-(phenyl)-N'-{p-(4-nitrobenzoylaminosulfonyl)}phenylurea |
| 22 | N-(4-toluyl)-N'-{p-(2-naphthoylaminosulfonyl)}phenylurea |
| 23 | N-(3-toluyl)-N'-{p-(3-toluoylaminosulfonyl)}phenylurea |
| 24 | N-(4-toluyl)-N'-{p-(4-hydroxybenzoylaminosulfonyl)}phenylurea |
| 25 | N-(4-toluyl)-N'-{p-(4-nitrobenzoylaminosulfonyl)}phenylurea |
| 26 | N-(phenyl)-N'-{p-(4-toluoylaminosulfonyl)}phenylthiourea |
| 27 | N-(phenyl)-N'-{p-(2-naphthoylaminosulfonyl)}phenylthiourea |
| 28 | N-(phenyl)-N'-{p-(4-hydroxybenzoylaminosulfonyl)}phenylthiourea |
| 29 | N-(phenyl)-N'-{p-(4-methoxybenzoylaminosulfonyl)}phenylthiourea |
| 30 | N-(4-toluyl)-N'-{p-(2-naphthoylaminosulfonyl)}phenylurea |
| 31 | N-(3-toluyl)-N'-(p-benzoylaminosulfonyl)phenylthiourea |
| 32 | N-(3-toluyl)-N'-{p-(4-toluoylaminosulfonyl)}phenylthiourea |

TABLE 3

Quality test results

| Test No. | (1) Dynamic color density | Heat resistance (2) Untreated | Treated | Retention (%) | Water resistance (3) Untreated | Treated | Retention (%) | Oil Resistance (4) Untreated | Treated | Retention (%) |
|---|---|---|---|---|---|---|---|---|---|---|
| Example 1 | | | | | | | | | | |
| 1 | 1.00 | 1.00 | 0.98 | 98 | 1.00 | 0.96 | 96 | 1.00 | 0.98 | 98 |
| 2 | 1.02 | 1.02 | 0.98 | 98 | 1.02 | 0.95 | 93 | 1.02 | 0.95 | 93 |

TABLE 3-continued

Quality test results

| | (1) | Heat resistance (2) | | | Water resistance (3) | | | Oil Resistance (4) | | |
|---|---|---|---|---|---|---|---|---|---|---|
| Test No. | Dynamic color density | Untreated | Treated | Retention (%) | Untreated | Treated | Retention (%) | Untreated | Treated | Retention (%) |
| 3 | 1.03 | 1.03 | 1.03 | 100 | 1.03 | 1.02 | 99 | 1.03 | 1.02 | 99 |
| 4 | 1.05 | 1.05 | 1.02 | 97 | 1.05 | 0.92 | 88 | 1.05 | 0.92 | 88 |
| 5 | 1.04 | 1.04 | 1.00 | 96 | 1.04 | 0.89 | 86 | 1.04 | 0.88 | 85 |
| 6 | 1.03 | 1.03 | 1.01 | 98 | 1.03 | 0.90 | 87 | 1.03 | 0.89 | 89 |
| 7 | 1.00 | 1.00 | 0.96 | 96 | 1.00 | 0.91 | 91 | 1.00 | 0.91 | 91 |
| 8 | 1.01 | 1.01 | 0.97 | 96 | 1.01 | 0.92 | 91 | 1.01 | 0.92 | 91 |
| 9 | 1.02 | 1.02 | 0.98 | 96 | 1.02 | 0.90 | 88 | 1.02 | 0.93 | 91 |
| 10 | 1.03 | 1.03 | 1.02 | 98 | 1.03 | 0.93 | 90 | 1.03 | 0.92 | 89 |
| 11 | 1.04 | 1.04 | 1.02 | 98 | 1.04 | 0.95 | 91 | 1.04 | 0.89 | 86 |
| 12 | 1.05 | 1.05 | 1.03 | 98 | 1.05 | 0.93 | 89 | 1.05 | 0.95 | 90 |
| 13 | 1.00 | 1.00 | 0.98 | 98 | 1.00 | 0.92 | 92 | 1.00 | 0.92 | 92 |
| 14 | 1.01 | 1.01 | 0.98 | 97 | 1.01 | 0.94 | 93 | 1.01 | 0.89 | 88 |
| 15 | 1.02 | 1.02 | 0.99 | 97 | 1.02 | 0.97 | 95 | 1.02 | 0.90 | 88 |
| 16 | 1.05 | 1.05 | 1.03 | 98 | 1.05 | 0.98 | 93 | 1.05 | 0.95 | 91 |

TABLE 4

Quality test results

| | (1) | Heat resistance (2) | | | Water resistance (3) | | | Oil Resistance (4) | | |
|---|---|---|---|---|---|---|---|---|---|---|
| Test No. | Dynamic color density | Untreated | Treated | Retention (%) | Untreated | Treated | Retention (%) | Untreated | Treated | Retention (%) |
| Example 1 | | | | | | | | | | |
| 17 | 1.03 | 1.03 | 1.01 | 98 | 1.03 | 0.90 | 87 | 1.03 | 0.89 | 89 |
| 18 | 1.00 | 1.00 | 0.96 | 96 | 1.00 | 0.91 | 91 | 1.00 | 0.91 | 91 |
| 19 | 1.05 | 1.05 | 1.03 | 98 | 1.05 | 1.00 | 95 | 1.05 | 1.00 | 95 |
| 20 | 1.02 | 1.02 | 0.98 | 96 | 1.02 | 0.90 | 88 | 1.02 | 0.93 | 91 |
| 21 | 1.03 | 1.03 | 1.02 | 99 | 1.03 | 0.93 | 90 | 1.03 | 0.92 | 89 |
| 22 | 1.04 | 1.04 | 1.02 | 98 | 1.04 | 0.95 | 91 | 1.04 | 0.89 | 86 |
| 23 | 1.05 | 1.05 | 1.03 | 98 | 1.05 | 0.93 | 89 | 1.05 | 0.95 | 90 |
| 24 | 1.00 | 1.00 | 0.98 | 98 | 1.00 | 0.92 | 92 | 1.00 | 0.92 | 92 |
| 25 | 1.01 | 1.01 | 0.98 | 97 | 1.01 | 0.94 | 93 | 1.01 | 0.89 | 88 |
| 26 | 1.02 | 1.02 | 0.99 | 97 | 1.02 | 0.97 | 95 | 1.02 | 0.90 | 88 |
| 27 | 1.05 | 1.05 | 1.03 | 98 | 1.05 | 0.98 | 93 | 1.05 | 0.96 | 91 |
| 28 | 1.04 | 1.04 | 1.02 | 98 | 1.04 | 0.98 | 84 | 1.04 | 0.96 | 92 |
| 29 | 1.03 | 1.03 | 1.02 | 99 | 1.03 | 0.93 | 90 | 1.03 | 0.96 | 93 |
| 30 | 1.02 | 1.02 | 0.99 | 97 | 1.02 | 0.94 | 92 | 1.02 | 0.91 | 89 |
| 31 | 1.00 | 1.00 | 0.98 | 98 | 1.00 | 0.91 | 91 | 1.00 | 0.90 | 90 |
| 32 | 1.01 | 1.01 | 0.96 | 95 | 1.01 | 0.97 | 96 | 1.01 | 0.92 | 91 |

TABLE 5

Quality test results

| Test No. | Color developer |
|---|---|
| Comparative Example 1 | |
| 33 | 4,4'-Isopropylidenediphenol |
| 34 | 4-Hydroxy-4-isopropoxydiphenylsulfone |
| 35 | Bis(4-hydroxyphenyl)acetic acid butyl ester |
| 36 | 4-Hydroxy-4'-n-propoxydiphenylsulfone |
| 37 | 4-Hydroxy-β-naphthalenesulfonate |
| 38 | 4-Hydroxy-4'-n-butoxydiphenylsulfone |

TABLE 6

| | (1) | Heat resistance (2) | | | Water resistance (3) | | | Oil Resistance (4) | | |
|---|---|---|---|---|---|---|---|---|---|---|
| Test No. | Dynamic color density | Untreated | Treated | Retention (%) | Untreated | Treated | Retention (%) | Untreated | Treated | Retention (%) |
| Comparative Example 1 | | | | | | | | | | |
| 33 | 1.12 | 1.12 | 0.53 | 47 | 1.12 | 0.67 | 60 | 1.12 | 0.59 | 53 |
| 34 | 1.11 | 1.11 | 0.53 | 48 | 1.11 | 0.68 | 61 | 1.11 | 0.53 | 48 |
| 35 | 1.14 | 1.14 | 0.57 | 50 | 1.14 | 0.67 | 59 | 1.14 | 0.57 | 50 |
| 36 | 1.12 | 1.12 | 0.54 | 48 | 1.12 | 0.69 | 62 | 1.12 | 0.57 | 51 |
| 37 | 1.10 | 1.10 | 0.56 | 51 | 1.10 | 0.69 | 63 | 1.10 | 0.55 | 50 |
| 38 | 1.09 | 1.09 | 0.53 | 49 | 1.09 | 0.70 | 64 | 1.09 | 0.56 | 51 |

TABLE 7

Quality test results

| Test No. | Color developer | Stabilizer |
|---|---|---|
| Example 2 | | |
| 39 | 4,4'-Isopropylidenediphenol | N-(benzenesulfonyl)-p-(phenylureilene)benzamide |
| 40 | 4-Hydroxy-4'-isopropoxy-diphenylsulfone | N-(4-toluenesulfonyl)-p-(phenylureilene)benzamide |
| 41 | Bis(4-hydroxyphenyl)acetic acid butyl ester | N-(benzenesulfonyl)-p-(phenylthioureilene)benzamide |

TABLE 8

| | (1) | Heat resistance (2) | | | Water resistance (3) | | | Oil Resistance (4) | | |
|---|---|---|---|---|---|---|---|---|---|---|
| Test No. | Dynamic color density | Untreated | Treated | Retention (%) | Untreated | Treated | Retention (%) | Untreated | Treated | Retention (%) |
| Example 2 | | | | | | | | | | |
| 39 | 1.08 | 1.08 | 0.82 | 76 | 1.08 | 0.87 | 81 | 1.08 | 0.81 | 75 |
| 40 | 1.07 | 1.07 | 0.79 | 74 | 1.07 | 0.86 | 80 | 1.07 | 0.79 | 74 |
| 41 | 1.08 | 1.08 | 0.76 | 70 | 1.08 | 0.84 | 78 | 1.08 | 0.78 | 72 |

The thermal recording sheet of the present invention has the following advantageous effects of storage stability of the recorded image.

(1) The recorded image is stable at high temperatures (heat resistance).

(2) The recorded image is stable and does not discolor when contacting with water (water resistance).

(3) The recorded image is stable and does not discolor when contacting with plasticizers, salad oil, vinegar, or the like (oil resistance).

What is claimed is:

1. A thermal recording sheet comprising a substrate having thereon a thermal color developing layer containing a colorless or pale colored, basic dye and an organic color developer as main ingredients, wherein said thermal color developing layer contains at least one compound of the following Formula (I)

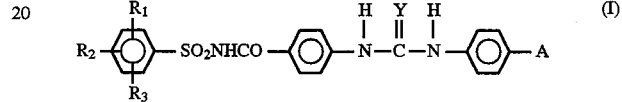

wherein

A denotes a hydrogen atom, an alkyl group of $C_1$ to $C_4$, an alkoxy group of $C_1$ to $C_4$, a hydroxy group or a nitro group, $R_1$, $R_2$, and $R_3$ are each independently a hydrogen atom, an alkyl group of $C_1$ to $C_4$, an alkoxy group of $C_1$ to $C_4$, a hydroxy group or a nitro group, and $R_1$ and $R_2$ may combine with each other to form an aromatic ring, and Y is a sulfur or an oxygen atom; or of the following Formula (II)

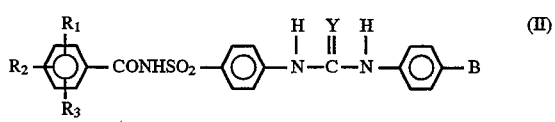

wherein

B denotes a hydrogen atom, an alkyl group of $C_1$ to $C_4$, an alkoxy group of $C_1$ to $C_4$, a hydroxy group or a nitro group, $R_1$, $R_2$, and $R_3$ are each independently a hydrogen atom, an alkyl group of $C_1$ to $C_4$, a hydroxy group or a nitro group, and $R_1$ and $R_2$ may combine with each other to form an aromatic ring, and Y is a sulfur or an oxygen atom.

2. The thermal recording sheet of claim 1, wherein said thermal color developing layer contains said at least one compound of the Formula (I) or the Formula (II) as an organic color developer in an amount of 1 to 8 parts based on 1 part of said basic dye.

3. The thermal recording sheet of claim 1, wherein said thermal color developing layer contains said at least one compound of the Formula (I) or the Formula (II) as a stabilizer in an amount of 0.25 to 3 parts based on 1 part of said basic dye.

* * * * *